United States Patent [19]

Dolejsi et al.

[11] 4,314,822

[45] Feb. 9, 1982

[54] METHOD FOR CHECKING THE INTENSITY OF DESTRUCTION OF MALIGNANT CELLS IN THE HUMAN BODY

[75] Inventors: Ivan Dolejší; Miloslav Spůr, both of Dvůr Králové, Czechoslovakia

[73] Assignee: Polytechna, podnik zahranicniho obchodu pro zprostredkovani technicke spoluprace, Prague, Czechoslovakia

[21] Appl. No.: 167,428

[22] Filed: Jul. 11, 1980

Related U.S. Application Data

[63] Continuation-in-part of Ser. No. 24,665, Mar. 28, 1979, abandoned.

[30] Foreign Application Priority Data

Jan. 9, 1979 [CS] Czechoslovakia ............... 199-79

[51] Int. Cl.$^3$ ............... G01N 31/02; G01N 33/50
[52] U.S. Cl. ............... 23/230 B; 424/9
[58] Field of Search ............... 23/230 B

[56] References Cited

U.S. PATENT DOCUMENTS

| | | | |
|---|---|---|---|
| 3,087,862 | 4/1963 | Penn | 23/230 B X |
| 3,615,229 | 10/1971 | Besch et al. | 23/230 B |
| 3,877,873 | 4/1975 | Winitz | 23/230 B |
| 3,999,944 | 12/1976 | Grosser et al. | 23/230 B |
| 4,043,757 | 8/1977 | Wagstaff | 23/230 B |
| 4,063,892 | 12/1977 | Vassile et al. | 23/230 B |
| 4,159,193 | 6/1979 | Gauntley et al. | 23/230 B |
| 4,169,676 | 10/1979 | Kaiser | 23/230 B X |

FOREIGN PATENT DOCUMENTS

609091  5/1978  U.S.S.R. ............... 23/230 B

*Primary Examiner*—Barry Richman

[57] ABSTRACT

A technique for monitoring the level of destruction of malignant cells in the human body. The technique involves the use of a higher aliphatic acid to esterify alkali alcoholates excreted into the urine during the course of the destruction of malignant cells.

8 Claims, 1 Drawing Figure

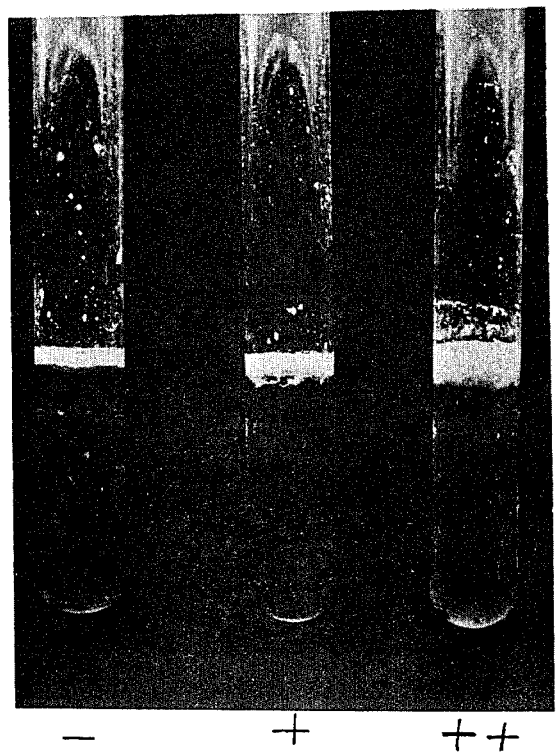

METHOD FOR CHECKING THE INTENSITY OF DESTRUCTION OF MALIGNANT CELLS IN THE HUMAN BODY

CROSS-REFERENCE

This application is a continuation-in-part of my copending application. Ser. No. 024,665, filed Mar. 28, 1979, and now abandoned.

This invention relates to a method for evaluating the destruction of malignant cells in the human body. More particularly, the present invention relates to a method for evaluating the results of treatment of malignant growths in humans by urine analysis.

Heretofore, methods for adequately monitoring the destruction of malignant growths in the human body have not been reported in the literature. Typically, the efficacy of treatment of malignant growths has been evaluated on the basis of indirect data, such data being obtained from laboratory tests and X-ray examinations. Unfortunately, the patient's condition can only be evaluated after long intervals of time and alterations in the therapy schedule frequently are too late. Thus, workers in the art have long sought a procedure for continuously monitoring a patient's condition, thereby permitting rapid alterations in therapy and achieving optimal effects with administered drugs and/or methods employed. In fact, optimal methodology would permit evaluating drugs administered and methods used within 24 hours of treatment.

In accordance with the present invention the prior art limitations have been effectively obviated and the noted goals achieved. More specifically, a method is described for detecting the presence of malignant growths in humans and for monitoring the effects of treatment of such growths, thereby permitting physicians to modify further treatment of a patient.

Briefly, the invention involves the use of a higher aliphatic acid, typically palmitic or stearic for detecting the intensity of destruction of malignant cells in the human body. The subject invention is based upon a discovery of a specific pathological lipid present in the membranes of malignant cells, such lipid being identified as triester 7, 12 dihydroxycholesterol. During the destruction of malignant cells, a series of substances is released that are in turn liquidated by common metabolic processes. This reaction, however, cannot affect the pathological substances as there is no corresponding desolvolytic system in the human body for them. In the case of the 7, 12 dihydroxycholesterol, the lipid is de-esterified by a hydrolysis reaction and converted into an alcoholate of an alkali metal, typically sodium or potassium. Following, the alcoholate is secreted in a dissociated form as an ion through the kidney filter into the urine. It is this substance which may be identified in urine by esterification of a higher aliphatic acid. Accordingly, the worker in the art is now capable of determining the quantity of separated alcoholate and, correspondingly, the quantity of malignant cells destroyed, based upon the quantity of the ester in a given volume of urine obtained from a given quantity of aliphatic acid. This technique is effected by esterification of the aliphatic acid by the steroid in a given quantity of urine at a pH ranging from 5.6 to 5.85 at a temperature within the range of 80° to 85° C.

The described technique now provides objective proof relating to the development of disease more rapidly than attainable heretofore and also permits a more objective approach to the therapy program.

In the operation of the present invention, the volume of liquids accepted and excreted in urine by a patient is measured during a 24 hour period. A given quantity of urine is taken as a sample (1% when more than 1 liter of urine is excreted, i.e., usually about 2–2.5 ml of urine).

Next, the pH value of the urine sample is adjusted to a value within the range of 5.6–5.85 by means of a pH indicator. This end is attained by adding 2 to 3 drops of an indicator such as bromothymol blue to the sample. In the event the pH of the sample exceeds 5.85, the sample may range in color from green to blue. The green hue indicates that the sample is slightly alkaline and it may be brought into the desired range by being buffered with a 0.1 mol solution of acetic acid until the sample acquires a yellow color. The blue color is indicative of a strongly alkaline solution and again requires acidification, preferably with acetic acid, until a yellow hue is obtained, so indicating that the pH value is suitable for testing.

Then, a higher aliphatic acid such as palmitic or stearic acid is added to the urine sample in an amount ranging from 0.01 to 0.008 grams of acid per milliliter of urine. The sample is then heated, as for example in a water bath, at a temperature ranging from 80° to 85° C. for a time period of the order of 20 minutes. Following, the sample is removed from the bath and permitted to cool to a temperature ranging from 13° to 30° C. over a time period of at least 30 minutes.

In the event malignant growths are not being destroyed in the human body, the aliphatic acid fails to react and solidifies on the surface of the sample in the form of a smooth ring or smooth droplets. However, the presence of a pathological steroid which is converted to an alkali trialcoholate is indicated by the presence of thread-like or rod-like formations that extend from the surface of the urine downward and these formations are caught by excess aliphatic acid. Analysis of the quantity and the dimensions of such formations permits judging of the quantity and character of the destruction products in the urine. The resultant ester may then be separated from the aliphatic acid by conventional techniques and the exact quantity of ester determined. Evaluation of the intensity of excretion of destruction products, i.e., the quantity of malignant growths destroyed, is made by comparing the quantity of ester produced relative to the quantity of excreted urine.

The single FIGURE of the drawing illustrates some urine samples into which an exact quantity of a higher aliphatic acid has been added in accordance with this invention.

The left test tube contains a treated urine sample marked "−", which means negative. The middle test tube contains a urine sample marked "+", which means slightly positive. The right test tube contains a urine sample marked "++" which means positive.

Several examples of the practice of the present invention are set forth below. It will be appreciated by those skilled in the art that these examples are merely for purposes of exposition and are not to be construed as limiting.

EXAMPLE 1

3 cubic centimeters of a sample of early morning urine were treated with 2 drops of bromothymol blue indicator. The pH value of the sample was in the alkaline range as indicated by a blue-green hue. The pH was then adjusted to a value of approximately 5.8, as indicated by a yellow hue by adding 0.1 molar acetic acid to the sample. Following 0.02 gram of palmitic acid was added to the sample which was then heated for 20 minutes at a temperature of about 80° C. Then, the sample was cooled for 30 minutes to 18° C. and the result of the test evaluated by comparing it with an evaluation scale.

EXAMPLE 2

The procedure of example 1 was repeated with the exception that 2.5 cc of urine were employed and 0.02 gram of stearic acid used instead of palmitic acid. Heating was effected at 85° C. and cooling for 30 minutes to a maximum of 15° C.

EXAMPLE 3

The procedure of example 2 was repeated with the exception that palmitic acid was employed and the pH value brought to 5.8. Cooling was effected for 30 minutes to 28° C.

The procedure described in the foregoing examples was employed in medical institutions, urine samples being taken from patients suffering from tumor diseases, non-tumor diseases and from persons with no evident symptoms of any disease. The test results were then compared with diagnosis and other data of the person who supplied the urine sample. Of 3000 urine samples taken and tested in accordance with the described procedure, 78.65% proved positive, that is, were correct in identifying the presence or absence of tumor diseases and those tested with patients having tumor diseases provided a useful technique for measuring the effect of treatment of malignant growths, that is, after the application of chemotherapy, immunotherapy, actinotherapy, and after operations on malignant growths.

In light of the fact that even with malignant growths without any prior treatment malignant cells are being destroyed, it is possible to employ the described technique for detecting cases of malignant growths in the population.

The application of the invention depends on expert evaluation of the test results. Thus, the absence of destruction products may indicate either the absence of malignant growths in the body, or an absolute failure of immunological reactions of the body (no destruction at all). Accordingly, evaluation of the test results by an expert is required.

Summarizing, the test of the invention has been found highly reliable with untreated persons.

The test of the invention is based on the detection of products obtained from pathological malignant cells. In the event the natural function of the malignant cells is dampened as, for example, by cytostatics, then the neoplasm does no longer produce any or fewer destroyed malignant cells and the test of this invention for detecting the neoplasm is no longer suitable.

A surgical intervention does not directly influence the test reliability. To the contrary, a test carried out after a surgical operation can fully prove the success or failure of such an operation. Negative results would show that the malignant tissue has been fully removed, whereas positive results after surgical operation suggests that in the respective organ metastases are present in addition to the malignant tumor.

However, the test reliability is fully restored with all treated patients as soon as the direct effect of cytostatics has dissipated or as soon as lesions or necroses caused by actinotherapy have fully healed.

In summary the results of the test of the invention must be evaluated by experts.

We claim:

1. Method for monitoring the destruction of malignant cells in the human body by determining the presence of alcoholate metabolites of malignant cells secreted in urine by the human body which comprises the steps of
   (a) adding a predetermined quantity of an aliphatic acid selected from the group consisting of palmitic and stearic acid to a urine sample, the urine having a pH value within the range of 5.6–5.85, and
   (b) maintaining the resultant mixture at a temperature within the range of 80°–85° C. for a predetermined period of time; the presence of alcoholate metabolites of malignant cells being determined quantitatively by esterification of the aliphatic acid thereby.

2. Method in accordance with claim 1 wherein said aliphatic acid is palmitic acid.

3. Method in accordance with claim 1 wherein said aliphatic acid is stearic acid.

4. Method in accordance with claim 1 wherein said aliphatic acid is added to the urine sample in an amount ranging from 0.01 to 0.008 grams per milliliter of urine.

5. Method in accordance with claim 1 wherein heating is effected for a time period of the order of 20 minutes.

6. Method in accordance with claim 5 wherein said heating is followed by cooling to a temperature ranging from 13°–30° C. for a time period of the order of 30 minutes.

7. Method in accordance with claim 1 wherein the pH is measured by means of an indicator and adjusted by means of a buffer.

8. Method in accordance with claim 7 wherein the urine is buffered with a 0.1 mol solution of acetic acid.

* * * * *